United States Patent [19]

Hesse

[11] Patent Number: Plant 6,156

[45] Date of Patent: Apr. 19, 1988

[54] CHRYSANTHEMUM PLANT NAMED YELLOW FROSTY

[75] Inventor: Peter S. Hesse, Bradenton, Fla.

[73] Assignee: Ball PanAm Plant Company, Parrish, Fla.

[21] Appl. No.: 873,791

[22] Filed: Jun. 12, 1986

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Yellow Frosty having flat capitulum form and single anemone type, yellow ray floret color, a prominence of lime-green to yellow disc florets, diameter of 20–40 mm. across face of capitulum, nine week flowering response, relatively short plant height when compared to the parent cultivar Frosty, semi-upright branching habit, and relatively small, deeply lobed and slightly serrated leaves.

1 Drawing Sheet

The present invention comprises a new and distinct cultivar of *Chrysanthemum morifolium*, Ramat., hereinafter referred to by the cultivar name Yellow Frosty.

Yellow Frosty was originated from a mutation resulting from a controlled radiation program involving the parent cultivar Frosty in Parrish, Fla., in 1982. The purpose of the radiation program was to expand the color range of Frosty, disclosed in U.S. Plant Pat. No. 5,491. The mutation originated as a single petal in the petalage of an irradiated plant of Frosty and was recovered by growing the petal in tissue culture.

Yellow Frosty was discovered in such form and selected by Peter S. Hesse in November of 1982 in a controlled environment in Parrish, Fla.

The first act of asexual reproduction of Yellow Frosty was accomplished when vegetative cuttings were taken from a plant grown from the initial selection in September of 1983 in a controlled environment in Parrish, Fla. by a technician working under formulations established and supervised by applicant. Horticultural examination of selected units initiated in December of 1983 has demonstrated that the combination of characteristics as herein disclosed for Yellow Frosty are firmly fixed and are retained through successive generations of asexual reproduction.

Yellow Frosty has not been observed under all possible environmental conditions. The phenotype may vary significantly with variations in environment such as temperature, light intensity and day length. The following observations, measurements and comparisons describe plants grown in Parrish, Fla. under greenhouse conditions which approximate those generally used in commercial practice.

The following traits have been repeatedly observed and are determined to be basic characteristics of Yellow Frosty, which in combination distinguish this Chrysanthemum as a new and distinct cultivar:

1. Nine week flowering response.
2. Flat capitulum form, with approximately 25 ray florets appearing in each capitulum.
3. Single anemone flower type.
4. Yellow ray floret color.
5. Lime green (immature) to yellow (mature) disc floret color, with many individual discs appearing.
6. Diameter across the face of the capitulum is 20–40 mm.

7. Pot plant height above the edge of the pot of 26–30 cm.
8. Almost always shorter than the parent Frosty when grown in comparative side by side trials.
9. Semi-upright branching habit.
10. Approximately 3–5 breaks per pinch, thereby producing a full plant.
11. Leaves are deeply lobed and slightly serrated.
12. Leaves are relatively small, with the largest being about 4 cm. wide and 8 cm. long.

Of the many commercial cultivars known to the present inventor, the most similar in comparison to Yellow Frosty is the parent cultivar Frosty. In comparison to Frosty, Yellow Frosty principally differs from its parent by its bright yellow ray floret color and slightly shorter height when grown in comparative trials. Other characteristics of Yellow Frosty are generally similar to those same characteristics of Frosty.

The accompanying photographic drawing shows typical inflorescence and foliage characteristics of Yellow Frosty, with colors being as nearly true as possible with illustrations of this type. The photograph is in black and white except for one flower which has been colored to accurately depict the color of the ray and disc florets.

In the following description, color references are made to The Royal Horticultural Society Colour Chart. The color values were determined between 12:00 noon and 1:00 p.m. on May 21, 1986 under fluorescent light at Bradenton, Fla.

Classification:

*Botanical.*—*Chrysanthemum morifolium*, Ramat., cv Yellow Frosty.

*Commercial.*—Pot mum.

INFLORESCENCE

A. Capitulum:

*Form.*—Flat.

*Type.*—Anemone.

*Diameter Across Face.*—20–40 mm.

B. Corolla of ray florets:

*Color (general tonality from a distance of three meters).*—Bright yellow.

*Color (upper surface).*—5A.

*Color (under surface).*—5C.

C. Corolla of disc florets:
*Color* (*mature*).—Yellow.
*Color* (*immature*).—Lime green.

D. Reproductive organs:
*Androecium.*—Present in disc florets only; many.
*Gynoecium.*—Present in both ray and disc florets; many.

PLANT

A. General appearance:
*Height.*—26–30 cm. from edge of pot.

B. Foliage:
*Color* (*upper surface*).—147A.
*Color* (*under surface*).—147B.

*Shape.*—Deeply lobed and slightly serrated; generally elliptical.

I claim:

1. A new and distinct cultivar of Chrysanthemum plant named Yellow Frosty, as described and illustrated, and particularly characterized by its flat capitulum form and single anemone type, yellow ray floret color, prominence of its lime-green to yellow disc florets, diameter of 20–40 mm. across face of capitulum, nine week flowering response, relatively shorter plant height when compared to parent cultivar Frosty, semi-upright branching habit, and by its relatively small, deeply lobed and slightly serrated leaves.

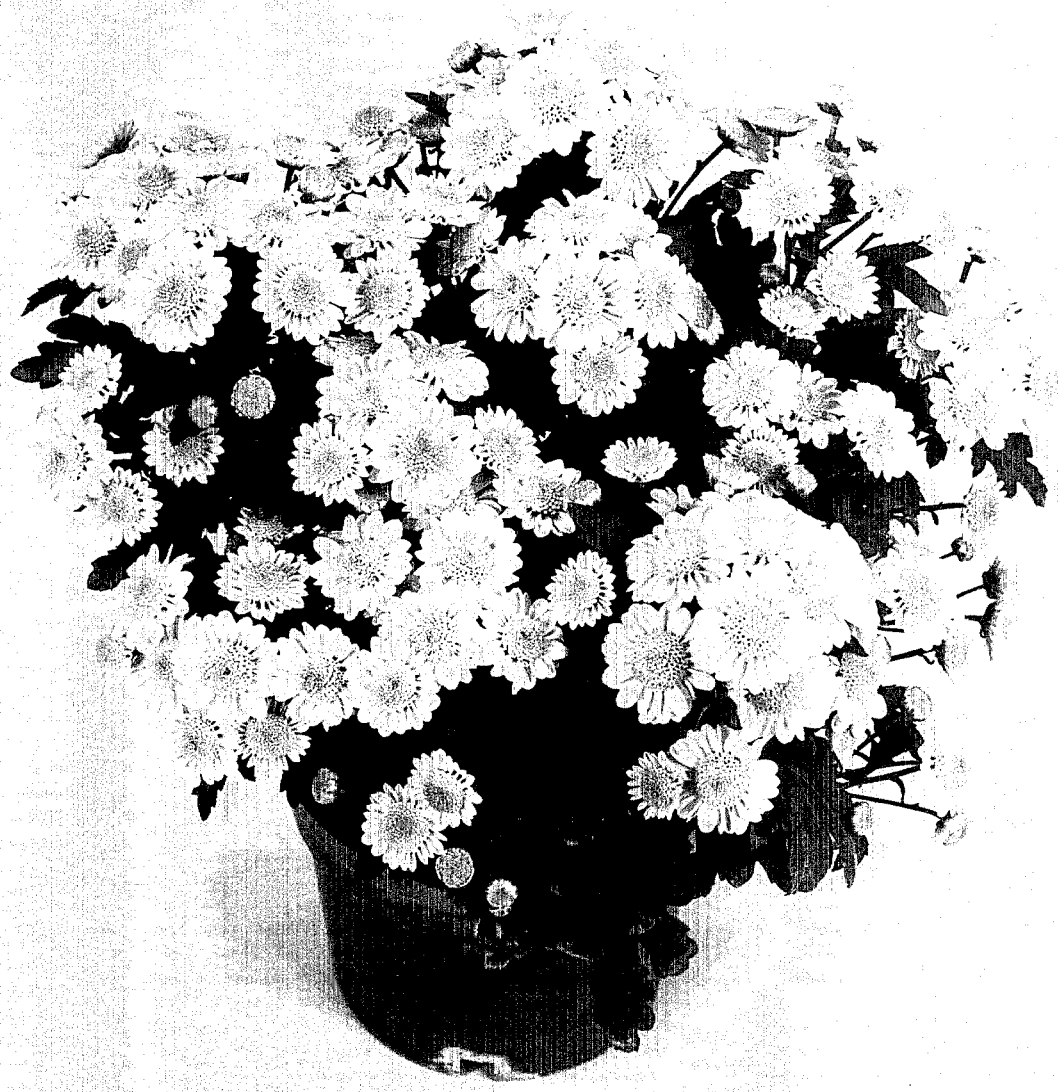

* * * * *